US012629133B2

(12) United States Patent     (10) Patent No.:   US 12,629,133 B2

Jiang et al.                 (45) Date of Patent:      May 19, 2026

(54) ULTRASONIC TRANSDUCER DEVICE AND MANUFACTURING METHOD THEREOF

(71) Applicant: Qisda Corporation, Taoyuan City (TW)

(72) Inventors: Fu-Sheng Jiang, Taoyuan City (TW); Pei-Lun Song, Taoyuan City (TW)

(73) Assignee: QISDA CORPORATION, Taoyuan City (TW)

( * ) Notice: Subject to any disclaimer, the term of this patent is extended or adjusted under 35 U.S.C. 154(b) by 0 days.

(21) Appl. No.: 18/908,954

(22) Filed: Oct. 8, 2024

(65) Prior Publication Data

US 2025/0127488 A1     Apr. 24, 2025

(30) Foreign Application Priority Data

Oct. 24, 2023    (TW) ................................. 112140571

(51) Int. Cl.
     *A61B 8/00*        (2006.01)
     *B06B 1/02*        (2006.01)
(52) U.S. Cl.
     CPC .......... *A61B 8/4483* (2013.01); *B06B 1/0292* (2013.01); *A61B 2562/12* (2013.01); *B06B 2201/76* (2013.01)

(58) Field of Classification Search
     CPC . A61B 8/4483; A61B 8/4494; A61B 2562/12; B06B 1/0292
     See application file for complete search history.

(56) References Cited

U.S. PATENT DOCUMENTS

| | | | | |
|---|---|---|---|---|
| 2010/0256498 A1* | 10/2010 | Tanaka | ................... | B06B 1/0292 600/459 |
| 2012/0256518 A1* | 10/2012 | Torashima | ............ | B06B 1/0292 310/300 |
| 2012/0256519 A1* | 10/2012 | Tomiyoshi | ............ | B06B 1/0292 310/300 |
| 2014/0010388 A1* | 1/2014 | Akiyama | ............. | H04R 19/005 381/191 |
| 2014/0313861 A1* | 10/2014 | Torashima | ............ | B06B 1/0292 367/181 |
| 2025/0100869 A1* | 3/2025 | Jiang | ....................... | G01N 29/32 |
| 2025/0128289 A1* | 4/2025 | Jiang | ....................... | B06B 1/0292 |
| 2025/0152137 A1* | 5/2025 | Jiang | ................... | A61B 8/4494 |
| 2025/0153220 A1* | 5/2025 | Jiang | ..................... | B06B 1/0662 |

* cited by examiner

*Primary Examiner* — J. San Martin

(57)          ABSTRACT

An ultrasonic transducer device and a manufacturing method thereof are provided. The ultrasonic transducer device includes a substrate, an ultrasonic oscillation unit and an upper insulating layer. The ultrasonic oscillation unit is disposed on the substrate and configured to emit or receive an ultrasonic wave. The ultrasonic wave has a resonant frequency. The upper insulating layer covers the ultrasonic oscillation unit. The upper insulating layer has a film thickness positively related to the resonant frequency.

10 Claims, 4 Drawing Sheets

100

108

108

106

102

104

ULTRASONIC TRANSDUCER DEVICE AND MANUFACTURING METHOD THEREOF

This application claims the benefit of Taiwan application Serial No. 112140571, filed Oct. 24, 2023, the subject matter of which is incorporated herein by reference.

BACKGROUND OF THE INVENTION

Field of the Invention

The invention relates in general to an ultrasonic device, and more particularly to an ultrasonic transducer device and a manufacturing method thereof.

Description of the Related Art

Along with the advance in medical technology, ultrasonic probing technology is getting more matured. Generally speaking, in the ultrasonic probing method, an ultrasonic signal is emitted to the underneath of the skin by a probe capable of emitting an ultrasonic signal. Then, the shape and position of an object under the skin and invisible to naked eyes are determined for various medical purposes by the probe according to the reflected ultrasonic signal.

Also, as the quality requirement of ultrasonic images is getting higher and higher, the technology of inhibiting sidelobe effect using an ultrasonic transducer has become a mainstream in the technology field of the present invention. For instance, the sidelobe effect can be inhibited by changing the thickness of the piezoelectric material of the ultrasonic transducer. To resolve the influence of sidelobe effect on ultrasonic signal and image quality, the arrangement of the elements of the ultrasonic transducer device must be changed so that the ultrasonic signal can be more effectively emitted and received.

SUMMARY OF THE INVENTION

The invention is directed to an ultrasonic transducer device and a manufacturing method thereof for improving the quality of ultrasonic images.

According to one embodiment of the present invention, an ultrasonic transducer device is provided. The ultrasonic transducer device includes a substrate, an ultrasonic oscillation piece and an upper insulating layer. The ultrasonic oscillation piece is disposed on the substrate. The ultrasonic oscillation piece includes a plurality of ultrasonic oscillation units arranged along an axial direction and configured to emit a set of ultrasonic waves, wherein the set of ultrasonic waves has a set of resonant frequencies. The upper insulating layer covers the ultrasonic oscillation units. The upper insulating layer has a film thickness positively related to the set of resonant frequencies.

According to another embodiment of the present invention, a manufacturing method of an ultrasonic transducer device is provided. The method includes the following steps. A plurality of ultrasonic oscillation units are formed on a substrate, wherein the ultrasonic oscillation units arranged along an axial direction. An upper insulating layer is formed on the ultrasonic oscillation units, wherein the upper insulating layer has a film thickness, which diminishes from the central region towards the two lateral sides of the upper insulating layer.

The above and other aspects of the invention will become better understood with regard to the following detailed description of the preferred but non-limiting embodiment(s). The following description is made with reference to the accompanying drawings.

DETAILED DESCRIPTION OF THE INVENTION

Figure 1:
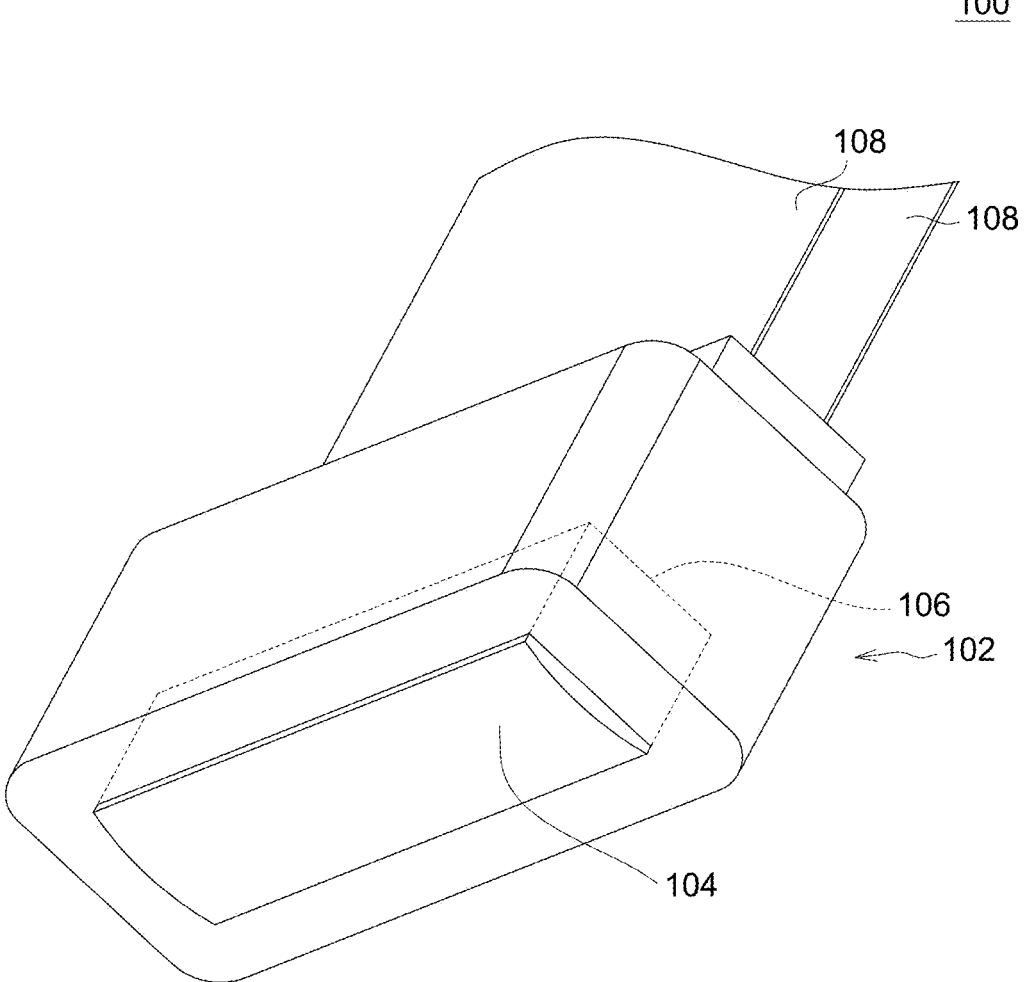
FIG. 1 is a schematic diagram of an ultrasonic probe according to an embodiment of the invention.

Referring to FIG. 1, a schematic diagram of an ultrasonic probe 100 according to an embodiment of the invention is shown. The ultrasonic probe 100 includes a casing 102, an acoustic lens 104, an ultrasonic transducer device 106 and a signal transmission line 108, wherein the ultrasonic transducer device 106 and the signal transmission line 108 are located inside the casing 102. The acoustic lens 104 is disposed at the front end of the casing 102. The ultrasonic transducer device 106 is configured to emit or receive an ultrasonic wave. The signal transmission line 108 is configured to transmit the acoustic signal to the ultrasonic transducer device 106 or transfer the acoustic signal received by the ultrasonic transducer device 106 back to the ultrasonic equipment. When contacting the user's skin, the ultrasonic probe 100 can emit or receive an ultrasonic signal via the acoustic lens 104 located at the front end of the casing 102 and transfers the electrical signal back to the ultrasonic equipment via the signal transmission line 108.

In an embodiment, the ultrasonic transducer device 106 can be a transducer formed of a plurality of capacitive micro-machined ultrasonic transducers (CMUT). In comparison to the conventional piezoelectric ultrasonic transducer, the CMUT has a 30% increase in bandwidth and better performance in terms of contrast strength, sharpness, and color saturation, therefore image resolution is greatly enhanced. Besides, the film layer of each ultrasonic oscillation unit 109 of the ultrasonic transducer device 106 can be formed on the substrate using a semiconductor process, which includes a film deposition process, a lithography process, an etching process, and a cleaning process. The film deposition process includes depositing a plurality of film layers on the substrate. The lithography process includes defining the pattern and shape of each film layer through the photo-resist layer, so that film layer stacks at a pre-determined position. The etching process includes removing redundant film layer to form a cavity in the film layer or form a groove. The cleaning process includes removing the photo-resist layer with an etching solution and other solution.

Figure 2:
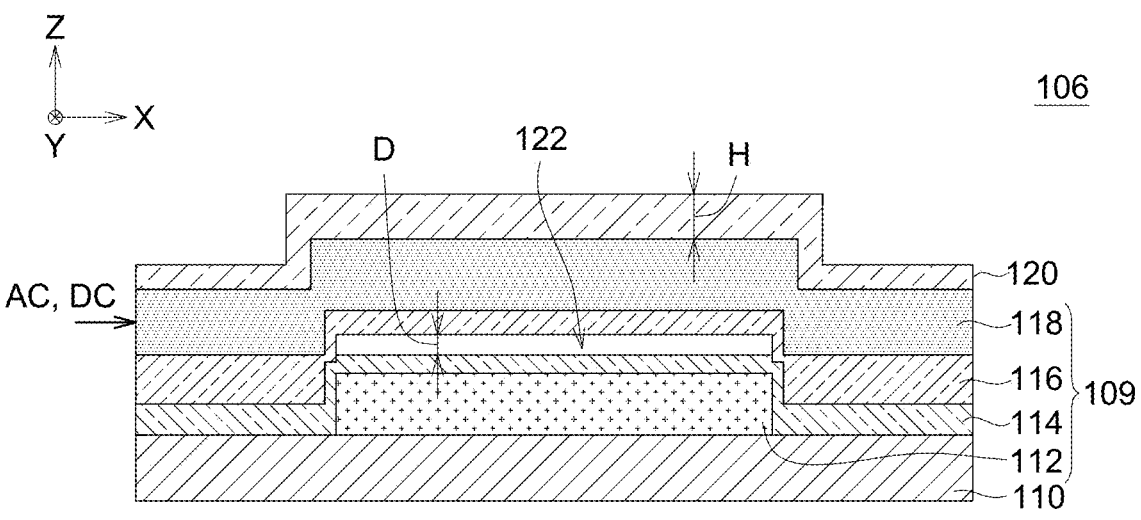
FIG. 2 is a cross-sectional view of an ultrasonic transducer device according to an embodiment of the invention.

Referring to FIG. 2, a cross-sectional view of an ultrasonic transducer device 106 according to an embodiment of the invention is shown. FIG. 2 illustrates only one ultrasonic oscillation unit 109. The ultrasonic transducer device 106 includes a substrate 110 and an ultrasonic oscillation unit 109. The ultrasonic oscillation unit 109 is also known as ultrasonic oscillator. The ultrasonic oscillation unit 109 is disposed on the substrate 110. The ultrasonic oscillation unit 109 includes a first electrode layer 112, a first insulating layer 114, a second electrode layer 118, a second insulating layer 116, and a cavity 122 interposed between the first insulating layer 114 and the second insulating layer 116.

Figure 3:
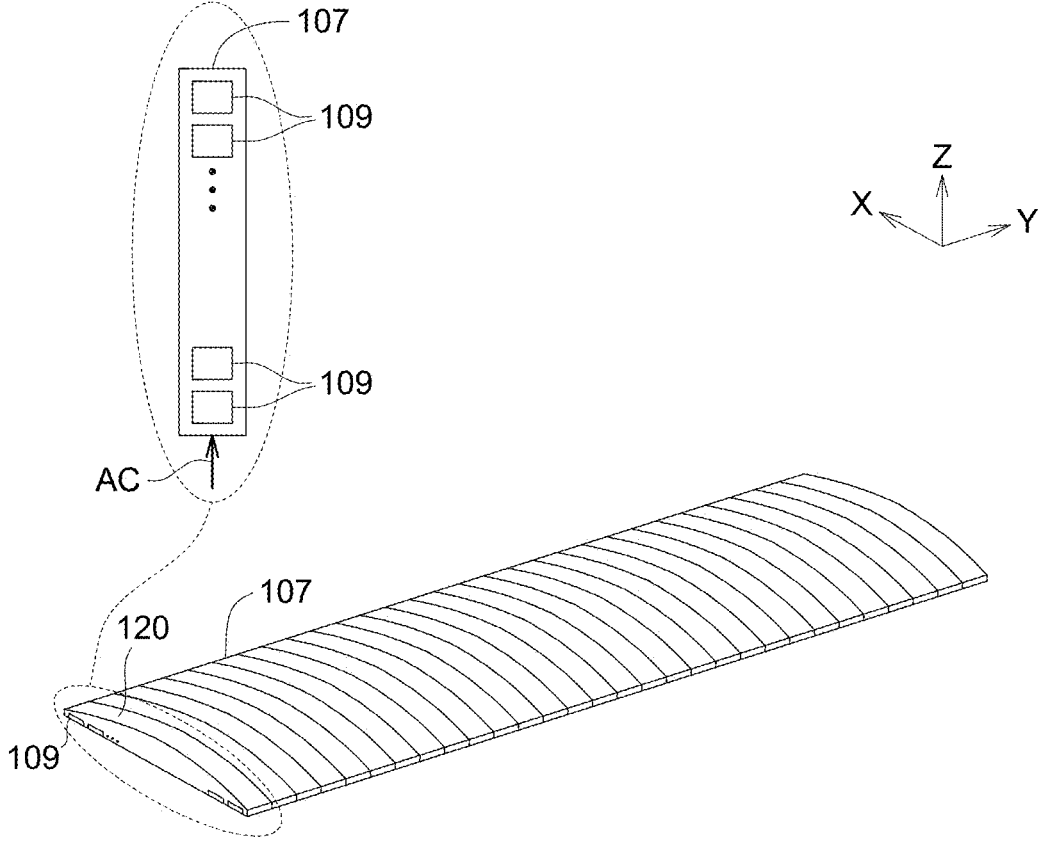
FIG. 3 is a schematic diagram of an ultrasonic transducer device according to an embodiment of the invention.

Although only one ultrasonic oscillation unit 109 is illustrated in FIG. 2, it can be understood that the ultrasonic transducer device 106 can be formed of a plurality of ultrasonic oscillation units 109 arranged as a one-dimensional array or a two-dimensional array. For instance, a plurality of ultrasonic oscillation units 109 can be arranged along the first direction (X-axis) and electrically connected to each other to form a one-dimensional ultrasonic oscillation piece 107 (as indicated in FIG. 3); or, a plurality of ultrasonic oscillation units 109 can be arranged along a first direction (X-axis) and a second direction (Y-axis) perpendicular to the first direction and electrically connected to each other to form a two-dimensional ultrasonic oscillation piece 107. As indicated in FIG. 3, a plurality of ultrasonic oscillation pieces 107 can be arranged along a long-axial direction (Y-axial direction) to form a set of ultrasonic oscillation pieces 107 in a strip shape. Each ultrasonic oscillation piece 107 can individually receive an alternate current voltage AC and vibrate, so that the ultrasonic signal can generate a resonant frequency in the cavity 122. Moreover, each ultrasonic oscillation piece 107 can also individually receive a sound pressure signal (such as an ultrasonic signal) and vibrate, so that the sound pressure signal can generate a resonant frequency in the cavity 122.

In an embodiment, the first electrode layer 112, a first insulating layer 114, a second insulating layer 116 and a second electrode layer 118 are sequentially stacked in a bottom-up manner. The first electrode layer 112 is formed on the substrate 110. The first insulating layer 114 covers the first electrode layer 112. The second insulating layer 116 covers the first insulating layer 114. A cavity 122 is interposed between the first insulating layer 114 and the second insulating layer 116, so that the first insulating layer 114 and the second insulating layer 116 are separated by an interval D. Firstly, a sacrificial layer is formed between the first insulating layer 114 and the second insulating layer 116. After structure stacking is completed, the sacrificial layer is etched with an etching solution to form a cavity 122 between the first insulating layer 114 and the second insulating layer 116. Then, the second electrode layer 118 is formed on the second insulating layer 116. In an embodiment, an upper insulating layer 120 can be formed on the second electrode layer 118 to protect the second electrode layer 118. The upper insulating layer 120, the first insulating layer 114 and the second insulating layer 116 cam be formed of identical or different materials. The first and second insulating layers 114, 116 can be formed of a silicon oxide (such as $SiO_2$), a nitride (such as SiN), a nitrogen oxide or any other suitable dielectric insulating materials.

In an embodiment, the cavity 122 of the ultrasonic oscillation unit 109 is interposed between the first electrode layer 112 and the second electrode layer 118. The first electrode layer 112 may be a grounding layer. The second electrode layer 118 may be a signal layer configured to receive an alternate current voltage AC and/or a direct current voltage DC signal. For instance, the second electrode layer 118 is driven by a direct current voltage to recess with respect to the first electrode layer 112, so that the first insulating layer 114 and the second insulating layer 116 become closer. Or, the second electrode layer 118 can be driven by an alternate current voltage AC or an external sound pressure to vibrate and generate an ultrasonic signal. The pulse period of the alternate current voltage AC can determine the resonant frequency of the outputted ultrasonic signal, so that the generated ultrasonic signals can have different frequencies.

In an embodiment, the resonant frequency of the ultrasonic signal in the cavity 122 is related to the dimension of the cavity 122 as well as the thicknesses of the second electrode layer 118, the second insulating layer 116 and the upper insulating layer 120. The dimension of the cavity 122 can be 40 μm×40 μm; the thickness of the second electrode layer 118 and the thickness of the second insulating layer 116 range between 1 μm-2 μm; the film thickness H of the upper insulating layer 120 ranges between 500 Å-18000 Å. Preferably, the film thickness H ranges between 4500 Å-9000 Å, but the present invention is not limited thereto. In the present embodiment, since the resonant frequency of the ultrasonic signal in the cavity 122 is related to the film thickness H of the upper insulating layer 120, when the film thickness H of the upper insulating layer 120 changes, the resonant frequency will change accordingly, and the resonant frequency generated by each ultrasonic oscillation unit 109 will be different.

Refer to FIG. 2. The upper insulating layer 120 covers the ultrasonic oscillation unit 109. The upper insulating layer 120 has a film thickness H, such as ranging between 4500 Å-9000 Å. The film thickness H is positively related to the resonant frequency. Refer to FIG. 3. The upper insulating layer 120 covers the ultrasonic oscillation pieces 107. Each ultrasonic oscillation piece 107 includes a plurality of ultrasonic oscillation units 109 arranged along an axial direction (such as X-axis) and configured to emit a set of ultrasonic waves having a set of resonant frequencies ranging between 12.3 MHz-8.2 MHz. The upper insulating layer 120 has a film thickness, such as ranging between 4500 Å-9000 Å. The film thickness is positively related to the set of resonant frequencies.

In an embodiment, the film thickness H of the upper insulating layer 120 diminishes from the central region of the upper insulating layer 120 towards the two lateral sides of the upper insulating layer 120. That is, the film thickness H of the upper insulating layer 120 reduces from 9000 Å to 4500 Å. The central region of the upper insulating layer 120 is thicker (film thickness H2, referring to FIG. 4A), and therefore the ultrasonic oscillation units 109 at central region can generate a higher resonant frequency. The two sides of the upper insulating layer 120 are thinner (film thickness H1, referring to FIG. 4B), and therefore the ultrasonic oscillation units 109 at two sides can generate a lower resonant frequency. For instance, when the film thickness H of the upper insulating layer 120 is 9000 Å, the ultrasonic wave can correspondingly generate a resonant frequency of 12.3 MHz in the cavity 122; when the film thickness H of the upper insulating layer 120 is 4500 Å, the ultrasonic wave can correspondingly generate a resonant frequency of 8.2 MHz in the cavity 122, but the present invention is not limited thereto.

Figures 4A, 4B:
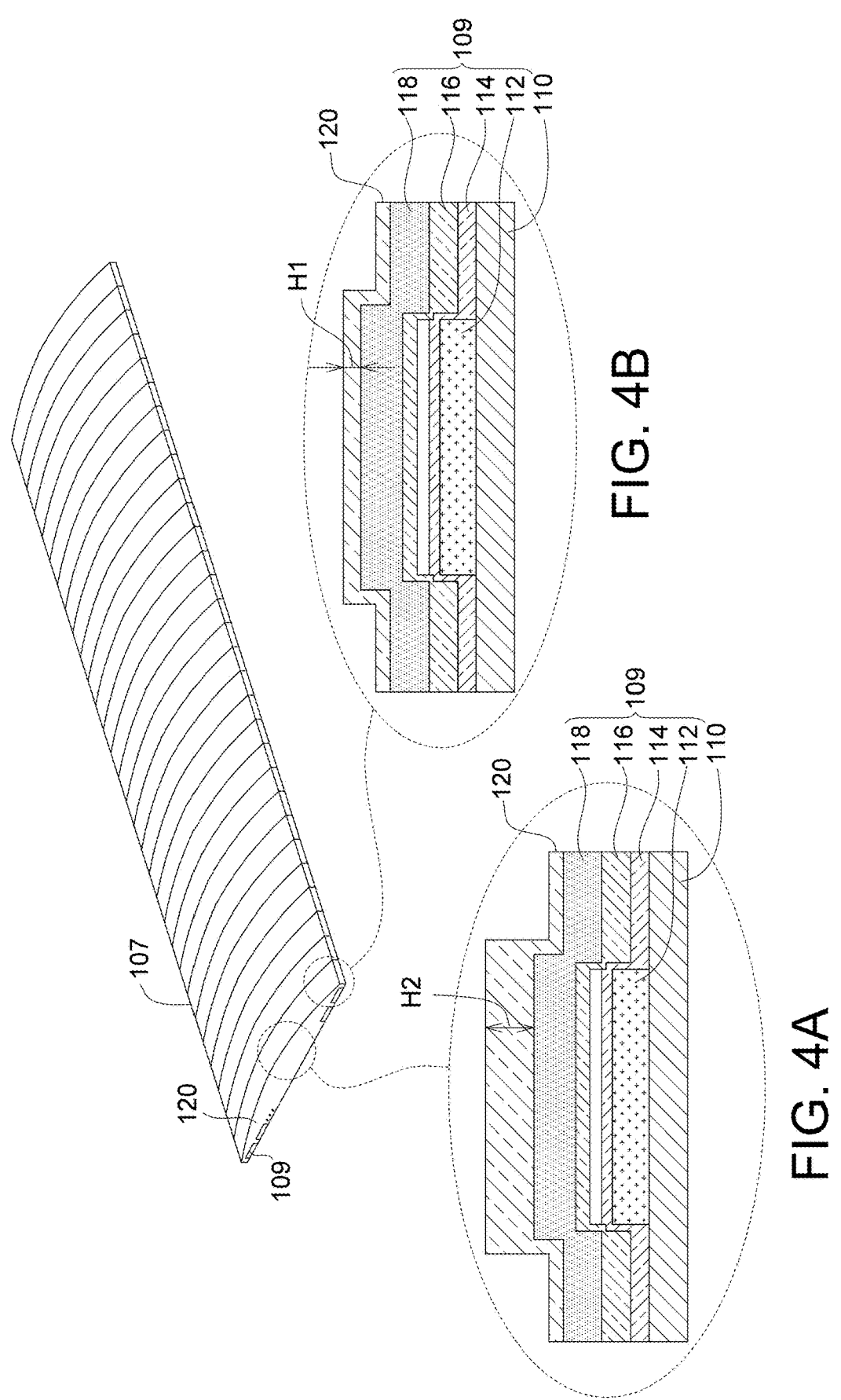
FIGS. 4A and 4B are schematic diagrams illustrating the upper insulating layer of FIG. 3 having different thicknesses.

Refer to FIG. 3 and FIGS. 4A and 4B. FIGS. 4A and 4B are schematic diagrams illustrating the upper insulating layer 120 of FIG. 3 having different thicknesses. In the X-axial direction, the film thickness of the upper insulating layer 120 diminishes from the central region of the ultrasonic oscillation piece 107 towards the two sides. That is, the film thickness H1 of the upper insulating layer 120 on two sides of the ultrasonic oscillation piece 107 is smaller than the film thickness H2 of the upper insulating layer 120 at the central region of the ultrasonic oscillation piece 107, that is, H1<H2. Thus, the film thickness H2 of the upper insulating layer 120 at the central region of the ultrasonic oscillation piece 107 is larger and the ultrasonic oscillation units 109 at the central region can generate a higher resonant frequency. The film thickness H1 of the upper insulating layer 120 on two sides of the ultrasonic oscillation piece 107 is smaller, and the ultrasonic oscillation units 109 at two sides can generate a lower resonant frequency. Thus, the resonant frequencies generated by each of the ultrasonic oscillation units 109 of the ultrasonic oscillation piece 107 are different.

Figure 5:
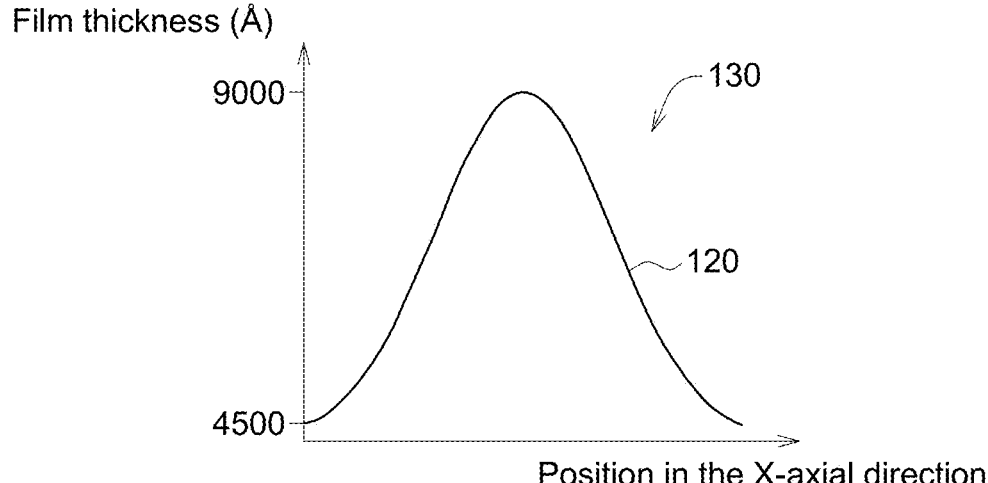
FIG. 5 is a schematic diagram of the distribution of the film thickness of the upper insulating layer in the X-axial direction corresponding to Gaussian distribution or Hanning distribution according to an embodiment of the invention.

Referring to FIG. 5, schematic diagrams of the distribution of the film thickness of the upper insulating layer 120 in the X-axial direction corresponding to Gaussian distribution 130 or Hanning distribution according to an embodiment of the invention is shown.

Refer to FIGS. 2 and 3. A manufacturing method of an ultrasonic transducer device 106 according to an embodiment of the invention is provided. Firstly, a plurality of ultrasonic oscillation units 109 is formed on a substrate 110, and the ultrasonic oscillation units 109 are arranged along an axial direction of an ultrasonic oscillation piece 107. The said arrangement is illustrated in FIG. 3, and the details are not repeated here. Next, an upper insulating layer 120 is formed on the ultrasonic oscillation units 109, and the upper insulating layer 120 has a film thickness, which diminishes from the central region towards the two lateral sides of the upper insulating layer 120. The arrangement of the upper insulating layer 120 is illustrated in FIGS. 4A and 4B.

In an embodiment, the upper insulating layer 120 can be formed at a pre-determined position with a pre-determined film thickness H using a semiconductor process. The semiconductor process includes a film deposition process, a lithography process, an etching process, and a cleaning process. The lithography process is also known as photolithography process. In the photolithography process, all patterns on the mask are firstly transferred to a photo-resist layer, and a part of the photo-resist layer is removed using a developing process to define the required pattern of the film layer. In the etching process, a part of the surface material is removed to form a film layer with different thicknesses using an isotropic etching or anisotropic etching method, such as dry etching, plasma etching, reactive ion etching or inductively coupled plasma etching, etc. Preferably, the upper insulating layer 120 is formed using an anisotropic etching method. In the dry etching process, a part of the material is removed by bombarding the surface of the film layer with positively charged ions. In the plasma etching process, the molecules of reactive gas are dissociated as reactive ions of the film material. The reactive ion etching method is a kind of etching method between sputter etching and plasma etching and possesses the advantages of anisotropic etching and acceptable selective etching.

In an embodiment, the upper insulating layer 120 can be formed using the abovementioned isotropic or anisotropic etching process, the pattern of the upper insulating layer 120 is determined by the transparency of a mask pattern in the photolithography process, the diffraction order of a mask pattern in the photolithography process, or the exposure intensity of a phase shift mask in the photolithography process. Through the transparency of the mask, the diffraction order of the mask or the exposure intensity of the phase shift mask in the photolithography process, the pattern of the upper insulating layer 120 that corresponds to the Gaussian distribution 130 and the Hanning distribution 131 can be formed.

According to the ultrasonic transducer device and the manufacturing method thereof disclosed in above embodiments of the invention, when the film thickness (such as decreases from 9000 Å to 4500 Å) of the upper insulating layer changes, the resonant frequency generated by each ultrasonic oscillation unit of the ultrasonic oscillation piece will be different, so that the influence of sidelobe effect on ultrasonic signals and image quality can be resolved and the resolution of ultrasonic image can be increased.

While the invention has been described by way of example and in terms of the preferred embodiment(s), it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. An ultrasonic transducer device, comprising:
a substrate;
a first ultrasonic oscillation unit disposed on the substrate and configured to emit or receive a first ultrasonic wave, wherein the first ultrasonic wave has a first resonant frequency;
a second ultrasonic oscillation unit disposed on the substrate and configured to emit or receive a second ultrasonic wave, wherein the second ultrasonic wave has a second resonant frequency different from the first resonant frequency; and
an upper insulating layer covering the first and second ultrasonic oscillation units, wherein the upper insulating layer has a film thickness positively related to the resonant frequency the upper insulating layer has a first film thickness and a second film thickness, the first film thickness is related to the first resonant frequency, and the second film thickness is related to the second resonant frequency.

2. The ultrasonic transducer device according to claim 1, wherein each of the first and second ultrasonic oscillation units comprises a first electrode layer, a first insulating layer, a second electrode layer, a second insulating layer, and a cavity interposed between the first insulating layer and the second insulating layer; the first insulating layer and the second insulating layer are separated by an interval and are interposed between the first electrode layer and the second electrode layer.

3. The ultrasonic transducer device according to claim 1, wherein the first and second film thicknesses range between 500 Å-18000 Å.

4. The ultrasonic transducer device according to claim 1, wherein the upper insulating layer comprises silicon nitride or silicon oxide.

5. An ultrasonic transducer device, comprising:
a substrate;
an ultrasonic oscillation piece disposed on the substrate, wherein the ultrasonic oscillation piece comprises a plurality of ultrasonic oscillation units arranged along an axial direction and configured to emit a set of ultrasonic waves having a set of resonant frequencies, wherein a first ultrasonic oscillation unit of the plurality of ultrasonic oscillation units is configured to emit or receive a first ultrasonic wave, wherein the first ultrasonic wave has a first resonant frequency, and a second ultrasonic oscillation unit of the plurality of ultrasonic oscillation units is configured to emit or receive a second ultrasonic wave, wherein the second ultrasonic wave has a second resonant frequency different from the first resonant frequency; and
an upper insulating layer covering the ultrasonic oscillation units, wherein the upper insulating layer has a first film thickness and a second film thickness, the first film thickness is related to the first resonant frequency, and the second film thickness is related to the second resonant frequency.

6. The ultrasonic transducer device according to claim 5, wherein each of the first and second ultrasonic oscillation units comprises a first electrode layer, a first insulating layer, a second electrode layer, a second insulating layer and a cavity interposed between the first insulating layer and the second insulating layer; the first insulating layer and the second insulating layer are separated by an interval and are interposed between the first electrode layer and the second electrode layer.

7. The ultrasonic transducer device according to claim 5, wherein the first and second film thicknesses range between 500 Å-18000 Å.

8. The ultrasonic transducer device according to claim 5, wherein the upper insulating layer comprises silicon nitride or silicon oxide.

9. The ultrasonic transducer device according to claim 5, wherein the first and second film thicknesses diminish from a central region of the upper insulating layer towards two lateral sides of the upper insulating layer.

10. The ultrasonic transducer device according to claim 9, wherein a distribution of the first and second film thicknesses in the axial direction corresponds to Gaussian distribution or Hanning distribution.

\* \* \* \* \*